US012788930B2

(12) United States Patent
Fujita

(10) Patent No.: US 12,788,930 B2
(45) Date of Patent: Nov. 10, 2026

(54) OXYGEN ENRICHMENT DEVICE, CONTROL METHOD AND CONTROL PROGRAM

(71) Applicant: Teijin Pharma Limited, Tokyo (JP)

(72) Inventor: Norihiro Fujita, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 426 days.

(21) Appl. No.: 18/277,912

(22) PCT Filed: Mar. 1, 2022

(86) PCT No.: PCT/JP2022/008494
§ 371 (c)(1),
(2) Date: Aug. 18, 2023

(87) PCT Pub. No.: WO2022/186175
PCT Pub. Date: Sep. 9, 2022

(65) Prior Publication Data

US 2024/0131290 A1 Apr. 25, 2024
US 2024/0226487 A9 Jul. 11, 2024

(30) Foreign Application Priority Data

Mar. 2, 2021 (JP) ................................ 2021-032686

(51) Int. Cl.
*B01D 53/047* (2006.01)
*A61M 16/00* (2006.01)
(Continued)

(52) U.S. Cl.
CPC ...... *A61M 16/101* (2014.02); *A61M 16/0003* (2014.02); *B01D 53/0454* (2013.01);
(Continued)

(58) Field of Classification Search
CPC ........... A61M 16/101; A61M 16/0003; A61M 2016/1025; A61M 2202/0208;
(Continued)

(56) References Cited

U.S. PATENT DOCUMENTS 4,781,735 A 11/1988 Tagawa et al.
5,074,893 A * 12/1991 Hursey ............... B01D 53/047 95/98
(Continued)

FOREIGN PATENT DOCUMENTS

EP 0 699 467 A2 3/1996
EP 0 705 636 A1 4/1996
(Continued)

OTHER PUBLICATIONS

Japanese Office Action issued Nov. 7, 2023 in Application No. 2023-503848.
(Continued)

*Primary Examiner* — Frank M Lawrence, Jr.
(74) *Attorney, Agent, or Firm* — Sughrue Mion, PLLC

(57) ABSTRACT

Provided are an oxygen concentrator, a control method, and a control program capable of preventing a drop in pilot pressure supplied to a pilot type solenoid valve used in at least either of the supply flow path opening/closing unit or the exhaust flow path opening/closing unit. An oxygen concentrator capable of preventing a pressure drop in both cylinders in the pressure equalization step and, as a result, preventing a drop in pilot pressure supplied to a pilot type solenoid valve used in at least either of the supply flow path opening/closing unit or the exhaust flow path opening/closing unit, as well as a pressure drop in the adsorption cylinder, by starting pressurization in advance in the already depressurized adsorption cylinder before the pressure equalization step.

6 Claims, 4 Drawing Sheets

(51) Int. Cl.
*A61M 16/10* (2006.01)
*B01D 53/04* (2006.01)
*C01B 13/02* (2006.01)

(52) U.S. Cl.
CPC ............... *A61M 2016/1025* (2013.01); *A61M 2202/0208* (2013.01); *A61M 2205/3334* (2013.01); *B01D 2256/12* (2013.01)

(58) Field of Classification Search
CPC ....... A61M 2205/3334; B01D 53/0454; B01D 2256/12; B01D 2257/102; B01D 53/053; B01D 53/04; B01D 53/0415; B01D 53/0446; B01D 2259/40015; B01D 2259/40064; B01D 2253/108; B01D 2259/4533; B01D 53/047; C01B 13/0259; C01B 2210/0014; C01B 2210/0046; C01B 13/02
USPC ......... 96/115, 116, 121; 95/96–98, 103–105, 95/130; 128/204.18, 205.12
See application file for complete search history.

(56) References Cited

U.S. PATENT DOCUMENTS

| | | | | |
|---|---|---|---|---|
| 5,518,526 | A * | 5/1996 | Baksh | B01D 53/0476 95/122 |
| 5,656,068 | A | 8/1997 | Smolarek et al. | |
| 6,691,702 | B2 | 2/2004 | Appel et al. | |
| 8,394,171 | B2 * | 3/2013 | Elseviers | C01B 3/56 95/12 |
| 2010/0000408 | A1 * | 1/2010 | Haruma | C01B 3/382 95/97 |
| 2010/0116270 | A1 | 5/2010 | Edwards et al. | |
| 2017/0065926 | A1 | 3/2017 | Lee et al. | |
| 2019/0275458 | A1 * | 9/2019 | Marsh | B01D 53/047 |
| 2022/0305428 | A1 * | 9/2022 | Yehya | B01D 46/00 |
| 2024/0226487 | A9 * | 7/2024 | Fujita | A61M 16/0003 |

FOREIGN PATENT DOCUMENTS

| | | | |
|---|---|---|---|
| JP | 63-166702 | A | 7/1988 |
| JP | 08-257341 | A | 10/1996 |
| JP | 11-179133 | A | 7/1999 |
| JP | 11-207128 | A | 8/1999 |
| JP | 2002-079030 | A | 3/2002 |
| JP | 2004-560 | A | 1/2004 |
| JP | 2006-062932 | A | 3/2006 |
| JP | 2008-173284 | A | 7/2008 |
| JP | 2008-212206 | A | 9/2008 |
| JP | 2008-229493 | A | 10/2008 |
| JP | 2008-238076 | A | 10/2008 |
| JP | 2009-532184 | A | 9/2009 |
| JP | 2011-092622 | A | 5/2011 |
| JP | 2012-508074 | A | 4/2012 |
| JP | 2013-220979 | A | 10/2013 |

OTHER PUBLICATIONS

International Preliminary Report on Patentability with translation of Written Opinion of the International Searching Authority issued Aug. 29, 2023 in Application No. PCT/JP2022/008494.
Extended European Search Report dated Jul. 31, 2024, issued in European Application No. 22763230.4.
International Search Report for PCT/JP2022/008494 dated Apr. 26, 2022 [PCT/ISA/210].
Office Action issued Sep. 27, 2025 in Chinese Patent Application No. 202280018682.1.
Korean Office Action dated Oct. 2, 2025 in Application No. 10-2023-7030551.

* cited by examiner

[Fig. 1]
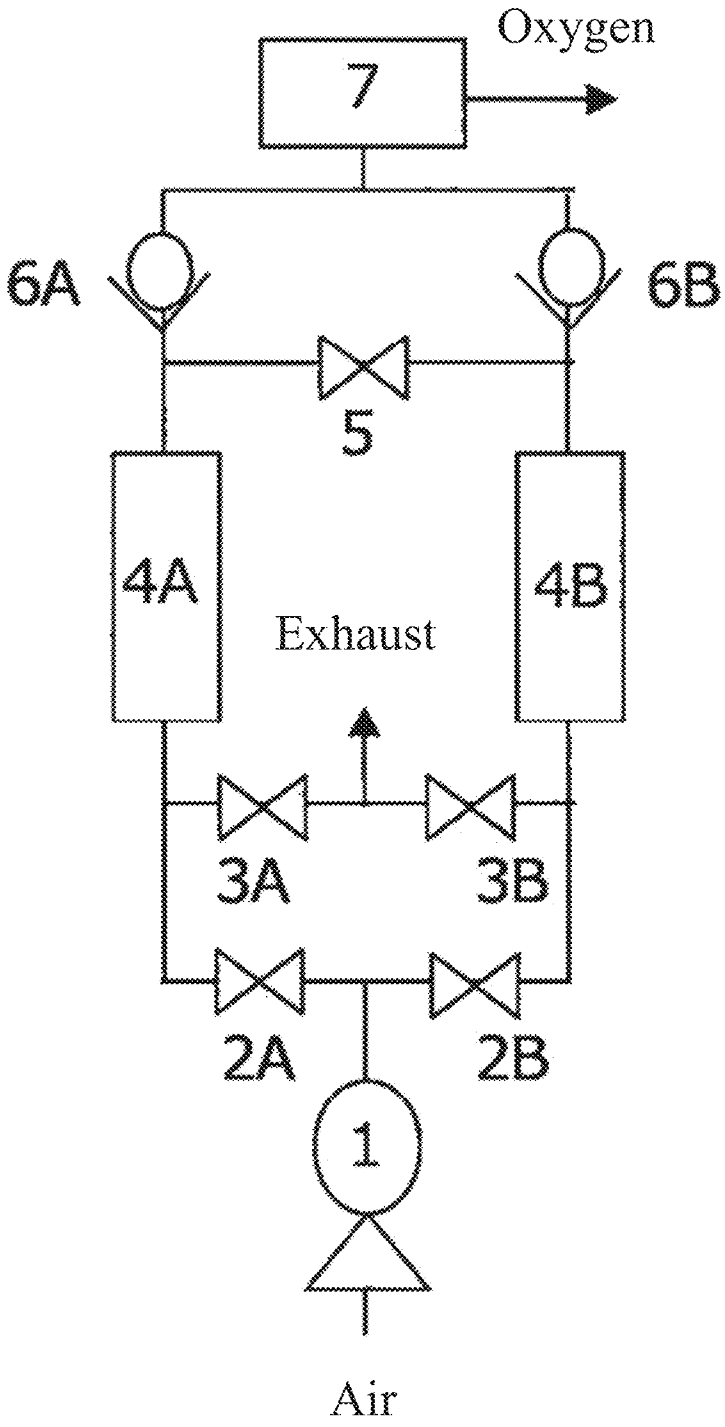

[Fig. 2(a)]Related Art

| | T1 | T2 | T3 | T4 | T5 | T6 |
|---|---|---|---|---|---|---|
| Cylinder 4A | Press Equal | Dprs Dsrp | Purge | Press Equal | Prss Adsrp | |
| Cylinder 4B | | Prss Adsrp | | | Dprs Dsrp | Purge |
| 2A (Supply) | Open | Closed | Closed | Open | Open | Open |
| 3A (Exhaust) | Closed | Open | Open | Closed | Closed | Closed |
| 2B (Supply) | Open | Open | Open | Open | Closed | Closed |
| 3B (Exhaust) | Closed | Closed | Closed | Closed | Open | Open |
| 5 (Communicate) | Open | Closed | Open | Open | Closed | Open |

[Fig.2(b)]

| | T1 | T2 | T3-1 | T3-2 | T4 | T5 | T6-1 | T6-2 |
|---|---|---|---|---|---|---|---|---|
| Cylinder 4A | Press Equal | Dprs Dsrp | Purge | Pre-Press | Press Equal | Prss Adsrp | | |
| Cylinder 4B | | Prss Adsrp | | | | Dprs Dsrp | Purge | Pre-Press |
| 2A (Supply) | Open | Closed | Closed | Closed | Open | Open | Open | Open |
| 3A (Exhaust) | Closed | Open | Open | Closed | Closed | Closed | Closed | Closed |
| 2B (Supply) | Open | Open | Open | Open | Open | Closed | Closed | Closed |
| 3B (Exhaust) | Closed | Closed | Closed | Closed | Closed | Open | Open | Closed |
| 5 (Communicate) | Open | Closed | Open | Open | Open | Closed | Open | Open |

Press Equal: Pressure equalization
Dprs Dsrp: Depressurized desorption
Prss Adsrp: Pressurized adsorption
Pre-Press: Pre-pressurization

[Fig. 3(a)] Related Art
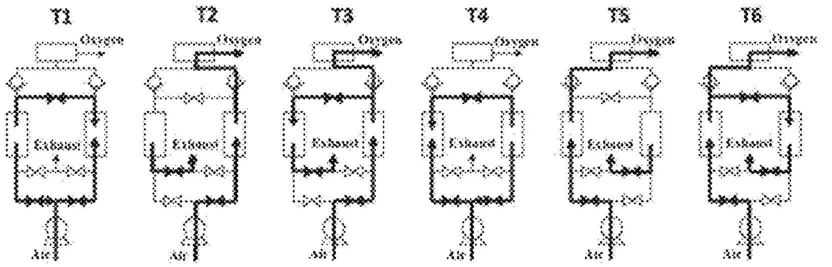
[Fig.3(b)]
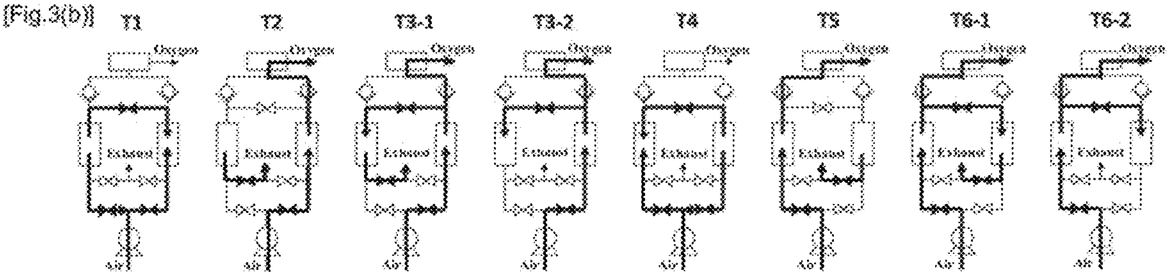

[Fig. 4(a)] Related Art
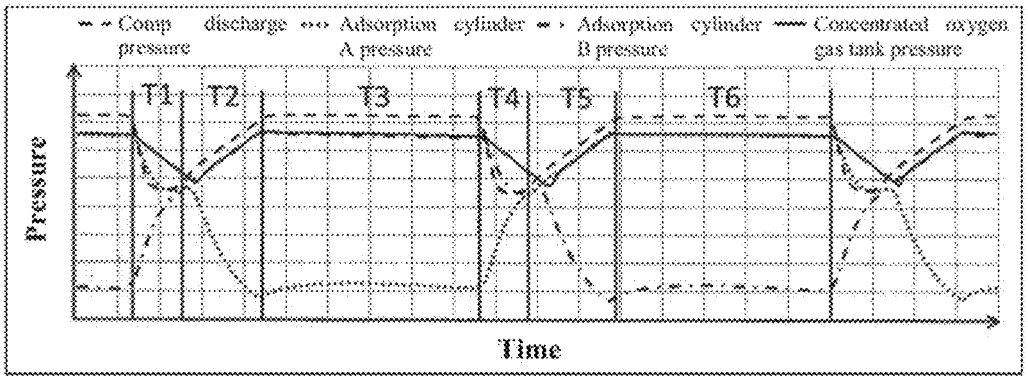
[Fig. 4(b)]
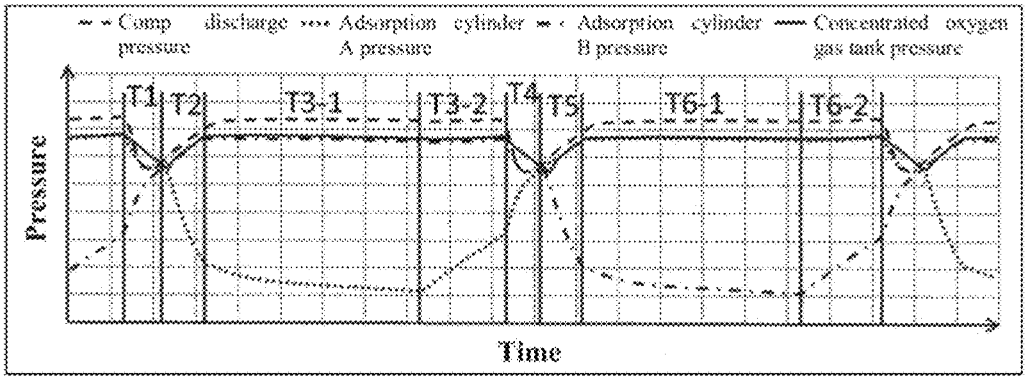

OXYGEN ENRICHMENT DEVICE, CONTROL METHOD AND CONTROL PROGRAM

CROSS REFERENCE TO RELATED APPLICATIONS

This application is a National Stage of International Application No. PCT/JP2022/008494 filed Mar. 1, 2022, claiming priority based on Japanese Patent Application No. 2021-032686 filed Mar. 2, 2021.

TECHNICAL FIELD

The present invention relates to an oxygen concentrator that separates and concentrates oxygen in the air and supplies it to a user. More specifically, with respect to an oxygen concentrator in which a pilot type solenoid valve is used in at least either of the supply flow path opening/closing unit or the exhaust flow path opening/closing unit, the present invention relates to an oxygen concentrator, a control method, and a control program capable of controlling the pressures in a plurality of adsorption cylinders so as to prevent a drop of the pilot pressure (the discharge pressure of the pressurized air supply unit, the internal pressure of the concentrated oxygen gas tank, or the internal pressure of the adsorption cylinder).

BACKGROUND ART

Conventionally, as one of the therapies for patients with respiratory diseases such as asthma and chronic obstructive pulmonary disease, there has been performed an oxygen therapy, in which a patient inhales oxygen gas or oxygen-enriched gas. In recent years, in order to improve a patient's quality of life (QOL), home oxygen therapy (HOT) of performing oxygen therapy at the patient's home has become mainstream. In home oxygen therapy, as an oxygen supply source for supplying oxygen gas to a patient, used is an oxygen concentrator that concentrates oxygen contained in air to produce oxygen gas and supplies the produced oxygen gas.

As oxygen concentrators, pressure swing adsorption (PSA) oxygen concentrators and vacuum pressure swing adsorption (VPSA) or vacuum swing adsorption (VSA) oxygen concentrators are widely used.

An oxygen concentrator has a plurality of adsorption cylinders filled with an adsorbent that selectively adsorbs nitrogen gas, and each of the plurality of adsorption cylinders repeats an adsorption step and a desorption step to produce concentrated oxygen gas, which is stored in a concentrated oxygen gas tank. The adsorption step is a step of producing oxygen gas from pressurized air by taking the pressurized air into the adsorption cylinder and adsorbing nitrogen gas on the adsorbent, and storing the produced concentrated oxygen gas in a concentrated oxygen gas tank. The desorption step is a step of depressurizing the adsorption cylinder by exposure to the atmosphere, and exhausting to the atmosphere the nitrogen gas adsorbed on the adsorbent in the adsorption step. The oxygen concentrator can continuously produce concentrated oxygen gas by repeating a rotation of adsorption step and desorption step among a plurality of adsorption cylinders.

There has been made the following proposals concerning the oxygen concentrator: in order to improve the efficiency of desorption in the desorption step, the concentrated oxygen gas produced in the adsorption cylinder during the adsorption step is flowed back from the end of the concentrated oxygen outlet side through the purge valve as purge gas to the adsorption cylinder in the desorption step, subsequently, in order to efficiently produce highly concentrated oxygen gas, the adsorption cylinder is depressurized to exhaust nitrogen and then is made communicate with the adsorption cylinder in the pressurization step via a pressure equalizing valve and the pressure is equalized (PTLs 1 and 2).

On the other hand, in order to suppress the power consumption of the oxygen concentrator, a method of controlling the compressor rotation speed to adjust the amount of air supplied (PTL 2) and a method of using a pilot type solenoid valve have been proposed (PTL 3). Since a pilot type solenoid valve operates a large main valve with a pilot pressure and thus switches the valve, the power consumption required for valve switching can be reduced even for a large effective flow passage cross section compared to a conventional direct-acting solenoid valve. In addition, since the flow rate loss can thus be reduced, which allows reduction of the discharge flow rate of the compressor, there can be reduced the power consumption required to drive the compressor, which is the mainly power-consuming device in the oxygen concentrator, supposedly resulting in power saving in the concentrator.

CITATION LIST

Patent Literature

[PTL 1] Japanese Unexamined Patent Application Publication No. 2002-79030

[PTL 2] Japanese Unexamined Patent Application Publication No. 11-207128

[PTL 3] Japanese Unexamined Patent Application Publication No. 2006-62932

SUMMARY OF INVENTION

Technical Problem

A pilot type solenoid valve requires supply of a pilot pressure for the switching operation, and, for example, when the pilot pressure is supplied by discharge pressure of the pressurized air supply unit, the discharge pressure of the pressurized air supply unit must be equal to or higher than the minimum operating pressure of the pilot type solenoid valve. The pilot pressure can be supplied by the internal pressure of the concentrated oxygen gas tank, the internal pressure of the adsorption cylinder, or the like, as well as the discharge pressure of the pressurized air supply unit. Therefore, the pilot pressure (the discharge pressure of the pressurized air supply unit, the internal pressure of the concentrated oxygen gas tank, or the internal pressure of the adsorption cylinder) must be equal to or higher than the minimum operating pressure of the pilot type solenoid valve.

However, in the case of pressure equalization by making the depressurized adsorption cylinder and the adsorption cylinder in the pressurization step communicate via the pressure equalizing valve, the cylinder pressure drops to the pressure under which the pressure is equalized between both adsorption cylinders, resulting also in drops of the discharge pressure of the pressurized air supply unit and the pressure in the concentrated oxygen gas tank. More specifically, since there is only a supply valve between the pressurized air supply unit and the adsorption cylinder, when the supply valve is open, the pressurized air supply unit and the adsorption cylinder communicate with each other, and the discharge pressure of the pressurized air supply unit will drop to the internal pressure of the adsorption cylinder.

In addition, in the running oxygen concentrator, the concentrated oxygen gas is always extracted from the concentrated oxygen gas tank at a predetermined flow rate; when the internal pressure of the adsorption cylinder is higher than the internal pressure of the concentrated oxygen gas tank, the gas automatically flows from the adsorption cylinder to the concentrated oxygen gas tank through the check valve provided between the adsorption cylinder and the concentrated oxygen gas tank, resulting in keeping the internal pressure at the same level between the adsorption cylinder and the concentrated oxygen gas tank; when the pressure equalization causes the internal pressure of the adsorption cylinder to drop below the pressure in the concentrated oxygen gas tank, the gas flow from the adsorption cylinder to the concentrated oxygen gas tank stops, and thus the pressure in the concentrated oxygen gas tank drops due to the continuous extraction of the concentrated oxygen gas at the predetermined flow rate, and further drops to the dropped internal pressure of the adsorption cylinder.

In addition, this problem appears prominently in the case of low flow rate operation and causes a bad effect: for example, although a low flow rate operation allows suppression of power consumption by lowering the rotation speed of the pressurized air supply unit and reducing the amount of supplied air in accordance with the oxygen extraction flow rate, the rotation speed of the pressurized air supply unit cannot be lowered below the level that satisfies the condition under which the minimum operating pressure or more of the pilot type solenoid valve is maintained. In addition, since the rotation speed of the pressurized air supply unit cannot be lowered further, air is supplied excessively with respect to the oxygen extraction flow rate, causing oxygen overadsorption resulting in another bad effect of oxygen concentration reduction.

As the present invention has been made in view of such circumstances, an object of the present invention is to solve the problem: during the pressure equalization step, by preventing a pilot pressure drop (the discharge pressure of the pressurized air supply unit, the internal pressure of the concentrated oxygen gas tank, or the internal pressure of the adsorption cylinder), to maintain the pilot pressure equal to or higher than the minimum operating pressure of the pilot type solenoid valve. Accordingly, an oxygen concentrator, a control method, and a control program are provided that enable control of the pressurized air supply unit rotation speed to suppress power consumption or to prevent the reduction in the oxygen concentration due to overadsorption of oxygen.

Solution to Problem

Accordingly, the present invention is an oxygen concentrator capable of preventing pressure drops in both cylinders in the pressure equalization step and, as a result, preventing a drop in pilot pressure supplied to a pilot type solenoid valve used in at least either of the supply flow path opening/closing unit or the exhaust flow path opening/closing unit, as well as a pressure drop in the adsorption cylinder, by starting pressurization in advance in the already depressurized adsorption cylinder before the pressure equalization step, thereby equalizing the pressure from the condition under which the cylinder pressure of the already depressurized adsorption cylinder is increased, and includes the following embodiments.

An oxygen concentrator according to one aspect of an embodiment of the present invention includes:

a plurality of adsorption cylinders filled with an adsorbent that preferentially adsorbs nitrogen over oxygen;

a pressurized air supply unit for supplying pressurized air to the adsorption cylinders;

a supply flow path opening/closing unit for connecting the pressurized air supply unit and each of the adsorption cylinders and opening/closing a gas flow path of pressurized air;

an exhaust flow path opening/closing unit for opening/closing a gas flow path for exhausting gas from each of the adsorption cylinders;

a concentrated oxygen gas tank for storing concentrated oxygen gas produced by the plurality of adsorption cylinders; and a communication flow path opening/closing unit for connecting an end of each of the adsorption cylinders on a concentrated oxygen gas outlet side and passing therethrough a part of produced concentrated oxygen gas, a pilot type solenoid valve being used in at least either of the supply flow path opening/closing unit or the exhaust flow path opening/closing unit, wherein the oxygen concentrator has a flow path opening/closing control unit for performing opening/closing control of the supply flow path opening/closing unit, the exhaust flow path opening/closing unit, and the communication flow path opening/closing unit, and the flow path opening/closing control unit performs control in each of the adsorption cylinders in such a way that the following steps are repeated in the order listed, (a) a pressurized adsorption step of adsorbing nitrogen in pressurized air on an adsorbent in the adsorption cylinder by supplying pressurized air, and extracting unadsorbed oxygen from an end on a concentrated oxygen gas outlet side of the adsorption cylinder;

(b) a pressure equalization step of equalizing pressures in the plurality of adsorption cylinders;

(c) a depressurized desorption step of depressurizing the adsorption cylinder, desorbing adsorbed nitrogen, and exhausting to outside air;

(d) a pre-pressurization step of starting in advance pressurization of an already depressurized adsorption cylinder; and (e) a pressure equalization step of equalizing pressures in the plurality of adsorption cylinders, and in such a way that, while (a) pressurized adsorption step is performed in one or in a group of adsorption cylinders, (c) depressurized desorption step and (d) pre-pressurization step are performed in the other or the other group of adsorption cylinders.

In the oxygen concentrator according to one aspect of an embodiment, the flow path opening/closing control unit, during (d) pre-pressurization step, preferably controls the exhaust flow path opening/closing unit from an adsorption cylinder during pre-pressurization to a closed state.

In the oxygen concentrator according to one aspect of an embodiment, the flow path opening/closing control unit, during (b) and (e) pressure equalization steps, preferably controls all of the supply flow path opening/closing units for the plurality of adsorption cylinders to an open state.

In the oxygen concentrator according to one aspect of an embodiment, the flow path opening/closing control unit, in the second half of (c) depressurized desorption step, preferably controls a part of concentrated oxygen gas produced in an adsorption cylinder during pressurized adsorption to be purged to an adsorption cylinder during depressurized desorption.

In the oxygen concentrator according to one aspect of an embodiment, the flow path opening/closing control unit, during (c) depressurized desorption step, preferably controls the communication flow path opening/closing unit to a closed state.

In the oxygen concentrator according to one aspect of an embodiment, the flow path opening/closing control unit, during (b) and (e) pressure equalization steps, may control the communication flow path opening/closing unit to a closed state.

A control method of an oxygen concentrator according to one aspect of an embodiment is for controlling pressures in a plurality of adsorption cylinders so as to prevent a drop in pilot pressure supplied to a pilot type solenoid valve used in at least either of the supply flow path opening/closing unit or the exhaust flow path opening/closing unit, wherein control is performed in each of the adsorption cylinders in such a way that the following steps are repeated in the order listed, a pressurized adsorption step of adsorbing nitrogen in pressurized air on an adsorbent in the adsorption cylinder by supplying pressurized air to the adsorption cylinder from a pressurized air supply unit, and extracting unadsorbed oxygen from an end on a concentrated oxygen gas outlet side of the adsorption cylinder;

a pressure equalization step of equalizing pressures in the plurality of adsorption cylinders;

a depressurized desorption step of depressurizing the adsorption cylinder, desorbing adsorbed nitrogen, and exhausting to outside air;

a pre-pressurization step of starting in advance pressurization of an already depressurized adsorption cylinder; and a pressure equalization step of equalizing pressures in the plurality of adsorption cylinders, and in such a way that, while a pressurized adsorption step is performed in one or in a group of adsorption cylinders, a depressurized desorption step and a pre-pressurization step are performed in the other or the other group of adsorption cylinders.

A control program of an oxygen concentrator according to one aspect of an embodiment is for controlling pressures in a plurality of adsorption cylinders so as to prevent a drop in pilot pressure supplied to a pilot type solenoid valve used in at least either of the supply flow path opening/closing unit or the exhaust flow path opening/closing unit, wherein a procedure of repeating the following procedures in the order listed is executed in each of the adsorption cylinders, a procedure of adsorbing nitrogen in pressurized air on an adsorbent in the adsorption cylinder by supplying pressurized air to the adsorption cylinder from a pressurized air supply unit, and extracting unadsorbed oxygen from an end on a concentrated oxygen gas outlet side of the adsorption cylinder (pressurized adsorption procedure);

a procedure of equalizing pressures in the plurality of adsorption cylinders (pressure equalization procedure);

a procedure of depressurizing the adsorption cylinder, desorbing adsorbed nitrogen, and exhausting to outside air (depressurized desorption procedure);

a procedure of starting in advance pressurization of an already depressurized adsorption cylinder (pre-pressurization procedure); and a procedure of equalizing pressures in the plurality of adsorption cylinders (pressure equalization procedure), and while a pressurized adsorption procedure is executed in one or in a group of adsorption cylinders, a depressurized desorption procedure and a pre-pressurization procedure are executed in the other or the other group of adsorption cylinders.

Advantageous Effects of Invention

In accordance with the present embodiment, during the pressure equalization step, prevention of a drop in pilot pressure (the discharge pressure of the pressurized air supply unit, the internal pressure of the concentrated oxygen gas tank, or the internal pressure of the adsorption cylinder) facilitates, even in the case of low flow rate operation, maintaining easily the pilot pressure equal to or higher than the minimum operating pressure of the pilot type solenoid valve, enabling control of the pressurized air supply unit rotation speed, and thus suppression of the power consumption.

In addition, decrease in the rotation speed of the pressurized air supply unit can reduce the amount of supplied air, which brings the effect of suppressing overadsorption of oxygen that occurs when the extraction flow rate is low with respect to the amount of supplied air.

The objects and advantages of the present invention may be recognized and obtained by means of the elements and combinations particularly pointed out in the CLAIMS. Both the general description above and the detailed description below are exemplary and explanatory, and are not for limiting the present invention as claimed.

BRIEF DESCRIPTION OF DRAWINGS

FIG. 1 is a functional block diagram of an oxygen concentrator according to an embodiment.

FIGS. 2(*a*) and 2(*b*) are diagrams showing opening/closing operations of a supply flow path opening/closing unit, an exhaust flow path opening/closing unit, and a communication flow path opening/closing unit controlled in the oxygen concentrator according to an embodiment. FIG. 2(*a*) shows the opening/closing operation of a general existing technology, and FIG. 2(*b*) shows an example of the opening/closing operation of the oxygen concentrator in an embodiment of the present invention.

FIGS. 3(*a*) and 3(*b*) are diagrams showing the gas flow by controlling opening/closing units of a supply flow path opening/closing unit, an exhaust flow path opening/closing unit, and a communication flow path opening/closing unit in the oxygen concentrator according to an embodiment. FIG. 3(*a*) shows the gas flow of a general existing technology, and FIG. 3(*b*) shows an example of the gas flow by the opening/closing operation of the oxygen concentrator according to an embodiment of the present invention.

FIGS. 4(*a*) and 4(*b*) are diagrams showing changes in the discharge pressure of the pressurized air supply unit (Comp discharge pressure), the internal pressure of each adsorption cylinder, and the internal pressure of the concentrated oxygen gas tank by controlling opening/closing units of a supply flow path opening/closing unit, an exhaust flow path opening/closing unit, and a communication flow path opening/closing unit in the oxygen concentrator according to an embodiment. FIG. 4(*a*) shows pressure changes in a general existing technology, and FIG. 4(*b*) shows an example of pressure changes in an oxygen concentrator according to an embodiment of the present invention.

DESCRIPTION OF EMBODIMENTS

Hereinafter, an oxygen concentrator, a control method, and a control program according to one aspect of the present disclosure will be described with reference to the drawings. However, it should be noted that the technical scope of the present disclosure is not limited to those embodiments, but extends to the invention described in the CLAIMS and equivalents thereof. In the following description and drawings, components having the same functional configuration are denoted by the same reference numerals, thereby omitting redundant description.

[Outline of Oxygen Concentrator According to Embodiment]

FIG. 1 is a functional block diagram of an oxygen concentrator according to an embodiment.

The oxygen concentrator includes a plurality of adsorption cylinders (4A and 4B) filled with an adsorbent that preferentially adsorbs nitrogen over oxygen, a pressurized air supply unit (1) supplying pressurized air to the adsorption cylinders, a pair of supply flow path opening/closing units (2A, 2B) that connects the pressurized air supply unit and the adsorption cylinders and opens/closes the gas flow paths of the pressurized air, a pair of exhaust flow path opening/closing units (3A, 3B) that opens/closes gas flow paths for atmospheric releasing and exhausting the adsorption cylinders, a concentrated oxygen gas tank (7) that stores concentrated oxygen gas produced by the plurality of adsorption cylinders, a communication flow path opening/closing unit (pressure equalizing/purging) (5) that connects the ends of each adsorption cylinder on the concentrated oxygen gas outlet side and passes therethrough a part of the produced concentrated oxygen gas, and a flow path opening/closing control unit that controls opening/closing of the supply flow path opening/closing units (2A, 2B), the exhaust flow path opening/closing units (3A, 3B), and the communication flow path opening/closing unit (pressure equalizing/purging) (5). Although here is shown a communication flow path opening/closing unit having one flow path, there may be employed a configuration having flow paths for pressure equalizing and purging independent of each other.

Opening and closing is controlled by the flow path opening/closing control unit for the supply flow path opening/closing units (2A, 2B), the exhaust flow path opening/closing units (3A, 3B), and the communication flow path opening/closing unit (pressure equalizing/purging) (5). The supply flow path opening/closing units (2A, 2B), the exhaust flow path opening/closing units (3A, 3B), and the communication flow path opening/closing units (pressure equalizing/purging) (5) are, for example, electromagnetic valves and control valves (solenoid valves, piezo valves), etc., and are controlled in accordance with a signal input from the flow path opening/closing control unit. The flow path opening/closing control unit has one or more processors and their peripheral circuits. The flow path opening/closing control unit controls integrally the operation of the oxygen concentrator, and is a processor such as a Micro Control Unit (MCU), for example.

The oxygen concentrator performs an oxygen gas production process of producing concentrated oxygen gas from raw material air and delivering the produced concentrated oxygen gas to the nostrils of a user, a patient using the oxygen concentrator.

Although FIG. 1 represents the components related to the concentrated oxygen gas production function, the oxygen concentrator may be equipped with an external air intake filter, a check valve, a pressure regulating valve, a flow rate setting unit, a humidifier, a filter, and the like.

First, raw material air is taken in from the outside through an air intake opening provided with an external air intake filter or the like for removing foreign matter such as dust. The pressurized air supply unit (1) compresses the air taken in through the external air intake filter to produce pressurized air, and the produced pressurized air is passed through the supply flow path opening/closing unit (2A, 2B) and supplied to either of the pair of adsorption cylinders (4A and 4B). The pressurized air supply unit (1) is also called a compressor, and examples thereof include an oscillating air compressor and a rotary air compressor such as a screw type, a rotary type, and a scroll type.

A pair of adsorption cylinders (4A and 4B) is filled with an adsorbent of zeolite that selectively adsorbs nitrogen gas over oxygen gas in pressurized air. Zeolite selectively adsorbs nitrogen gas contained by about 77% in the pressurized air supplied from the pressurized air supply unit (1).

A pair of adsorption cylinders (4A and 4B) adsorbs nitrogen gas and produces oxygen gas in the pressurized air supplied from the pressurized air supply unit (1) through the supply flow path opening/closing units (2A, 2B). While the adsorption cylinder (4A) produces oxygen gas, the adsorption cylinder (4B) exhausts the adsorbed nitrogen gas to the outside of the oxygen concentrator through the exhaust flow path opening/closing unit (3B). While the nitrogen gas adsorbed by the adsorption cylinder (4A) is exhausted to the outside of the oxygen concentrator through the exhaust flow path opening/closing unit (3A), the adsorption cylinder (4B) produces oxygen gas. Oxygen gas is produced alternately between a pair of adsorption cylinders (4A and 4B), enabling the oxygen concentrator to produce oxygen gas continuously. Although the oxygen concentrator is described using a pair of adsorption cylinders (4A and 4B) as an example, the oxygen concentrator according to an embodiment may have three or more adsorption cylinders. When three or more adsorption cylinders are provided, the operation is performed in such a way that the adsorption step and the desorption step can be repeated in turn among the plurality of adsorption cylinders. For example, in the case of a three-cylinder type with three adsorption cylinders (4A, 4B and 4C), the control is performed by switching the cylinders sequentially as follows: when the adsorption cylinder (4A) is in the adsorption step, a group of adsorption cylinders (4B and 4C) is in the desorption step; when the adsorption cylinder (4B) is in the adsorption step, a group of adsorption cylinders (4C and 4A) is in the desorption step; when the adsorption cylinder (4C) is in the adsorption step, a group of adsorption cylinders (4A and 4B) is in the desorption step.

The supply flow path opening/closing unit and/or the exhaust flow path opening/closing unit are pilot type solenoid valves. A pilot type solenoid valve switches the operation of a large main valve with a pilot pressure (air pressure). A supply source of the pilot pressure can be a discharge pressure of the pressurized air supply unit, an internal pressure of the concentrated oxygen gas tank, or an internal pressure of the adsorption cylinder, in which particularly the discharge pressure of the pressurized air supply unit, which is the supply source of air, is most utilized. The pilot pressure varies depending on the characteristics of the pilot type solenoid valve used, but the present specification shows an example where 40 kPa or more is required. The pilot pressure is permitted to temporarily drop below the minimum operating pressure of the pilot type solenoid valve as long as the pressure does not hinder the opening and closing of the pilot type solenoid valve. Although an oxygen concentrator is more efficient if both the supply flow path opening/closing unit and the exhaust flow path opening/closing unit are pilot type solenoid valves, also included in the problem to be solved in the present invention is a case in which either one is a pilot type solenoid valve.

A pair of check valves (6A and 6B) is provided between each of the pair of adsorption cylinders (4A and 4B) and the concentrated oxygen gas tank (7). Providing check valves (6A, 6B) between the adsorption cylinders (4A and 4B) and the concentrated oxygen gas tank (7) can prevent the concentrated oxygen gas from flowing back to the adsorption cylinder side when the internal pressure of the concentrated oxygen gas tank becomes higher than the internal pressure of the adsorption cylinder. The check valve (6A) is in an open state while the adsorption cylinder (4A) produces oxygen gas, allowing the concentrated oxygen gas produced by the adsorption cylinder (4A) to flow into the concentrated oxygen gas tank (7). In addition, the check valve (6B) is in a closed state while the nitrogen gas adsorbed by the adsorption cylinder (4B) is exhausted to the outside of the oxygen concentrator through the exhaust flow path opening/closing unit (3B), which prevents the concentrated oxygen gas stored in the concentrated oxygen gas tank (7) from being exhausted to the outside of the oxygen concentrator through the adsorption cylinder (4B).

The concentrated oxygen gas tank (7), also called a product tank, stores the oxygen gas produced by each of the pair of adsorption cylinders (4A and 4B). The internal pressure of the concentrated oxygen gas tank (7) fluctuates depending on the internal pressure change associated with the production of concentrated oxygen gas in each of the adsorption cylinders (4A and 4B). In order to keep, at a predetermined level, the pressure of the concentrated oxygen gas delivered from the concentrated oxygen gas tank (7) having internal pressure fluctuation associated with the production of concentrated oxygen gas, there is provided a pressure regulating valve, such as a pressure reducing valve.

The concentrated oxygen gas extracted from the concentrated oxygen gas tank (7) is controlled to flow at a predetermined flow rate by adjusting the opening of a solenoid valve of the flow rate control unit in accordance with the flow rate output signal input from the control unit.

The concentrated oxygen gas adjusted to the predetermined flow rate, from which foreign matter such as dust produced in the process of producing concentrated oxygen gas is removed by an air filter, is moderately moistened by a humidifier to prevent from nostrils to respiratory tract of the user from drying and supplied to the user from the end of the flow path such as a cannula.

The concentration and flow rate of the concentrated oxygen gas can be measured by connecting a concentration sensor and a flow rate sensor in the flow path of the concentrated oxygen gas between the air filter of the outlet filter and the humidifier.

[Control]

In the oxygen concentrator according to an embodiment, the pressure in the adsorption cylinder is controlled so as to prevent a drop in pilot pressure supplied to a pilot type solenoid valve used in at least either of the supply flow path opening/closing unit or the exhaust flow path opening/closing unit, and for this purpose, there is provided a flow path opening/closing control unit that performs opening/closing control of the supply flow path opening/closing units (2A, 2B), the exhaust flow path opening/closing units (3A, 3B), and the communication flow path opening/closing unit (5). The control of the pressure in the adsorption cylinder will be explained with reference to FIG. 2(*a*) to FIG. 4(*b*).

As described above, the oxygen concentrator can continuously produce concentrated oxygen gas by repeating a rotation of adsorption step and desorption step among a plurality of adsorption cylinders. First, along FIGS. 2(*a*)-2(*b*) and FIGS. 3(*a*)-(*b*), there will be described the opening/closing operations of the supply flow path opening/closing unit, the exhaust flow path opening/closing unit, and the communication flow path opening/closing unit controlled in the oxygen concentrator according to an embodiment, and the gas flow resulting from the controlled opening/closing operation of the supply flow path opening/closing unit, the exhaust flow path opening/closing unit, and the communication flow path opening/closing unit in the oxygen concentrator according to an embodiment.

FIG. 2(*a*) shows the opening/closing operation of a general existing technology, and FIG. 2(*b*) shows an example of the opening/closing operation of the oxygen concentrator in an embodiment of the present invention.

In T1, T4 of the example of FIG. 2(*b*), both adsorption cylinders (4A and 4B) are in a pressure equalization step, both supply flow path opening/closing units (2A, 2B) are in the open state, both exhaust flow path opening/closing units (3A, 3B) are in the closed state, and communication flow path opening/closing unit (5) is in the open state. The adsorption cylinders (4A and 4B) communicate with each other via supply flow path opening/closing units (2A, 2B) and communication flow path opening/closing unit (5) (see FIG. 3(*b*)), and thus are pressure-equalized. Even when the communication flow path opening/closing unit (5) is in the closed state, the pressure equalization can be achieved only by opening both supply flow path opening/closing units (2A, 2B). Here, even though the pressure equalization can be achieved when communication flow path opening/closing unit (5) is in the open state and only one of supply flow path opening/closing units is in the open state, making both supply flow path opening/closing units (2A, 2B) in the open state allows the pressure equalization to be achieved quickly. Note that T1, T4 correspond to "(b) a pressure equalization step of equalizing pressures in the plurality of adsorption cylinders" and "(e) a pressure equalization step of equalizing pressures in the plurality of adsorption cylinders" in the CLAIMS, respectively. The time for T1, T4 is preferably determined by the time until the pressures of the adsorption cylinder (4A) and the adsorption cylinder (4B) become the same, or may be shorter.

In the present specification, low flow rate operation is defined as performed with oxygen gas in the flow rate range of 0.1 LPM or more and less than 2.00 LPM.

T2/T5, as shown in FIG. 2(*b*), is a depressurized desorption step for one adsorption cylinder (T2_4A/T5_4B) and is a pressurized adsorption step for the other adsorption cylinder (T2_4B/T5_4A). In this case, with respect to the adsorption cylinder (T2_4A/T5_4B) in the depressurized desorption step, the supply flow path opening/closing unit (T2_2A/T5_2B) is in the closed state, the exhaust flow path opening/closing unit (T2_3A/T5_3B) is in the open state, and the communication flow path opening/closing unit (5) is in the closed state. On the other hand, with respect to the adsorption cylinder (T2_4B/T5_4A) in the pressurized adsorption step, the supply flow path opening/closing unit (T2_2B/T5_2A) is in the open state and the exhaust flow path opening/closing unit (T2_3B/T5_3A) is in the closed state. During the depressurized desorption step, in the adsorption cylinder (T2_4A/T5_4B), the pressure is decreased because the supply flow path opening/closing unit (T2_2A/T5_2B) becomes the closed state and the exhaust flow path opening/closing unit (T2_3A/T5_3B) becomes the open state and open to the air, rendering the nitrogen gas adsorbed on the adsorbent desorbed to be exhausted to the outside air (see FIG. 3(*b*)). The adsorption cylinder (T2_4B/T5_4A) in the pressurized adsorption step is pressurized by the supplied pressurized air and produces concentrated oxygen gas by adsorbing nitrogen in the air on the adsorbent in the adsorption cylinder (T2_4B/T5_4A), and the produced concentrated oxygen gas is delivered to the concentrated oxygen gas tank (7) via the check valve (T2_6B/T5_6A) (see FIG. 3(*b*)). Although the time for T2/T5 is not particularly limited as long as a required oxygen concentration can be obtained, the time is preferably lengthened for further desorption of the adsorbed nitrogen until the internal pressure of the adsorption cylinder becomes as low as possible.

T3-1/T6-1, as shown in FIG. 2(*b*), is a purge step for one adsorption cylinder (T3-1_4A/T6-1_4B), during which a part of the concentrated oxygen gas produced in the adsorption cylinder during pressurized adsorption is supplied to the adsorption cylinder during depressurized desorption. The other adsorption cylinder (T3-1_4B/T6-1_4A) continues the pressurized adsorption step of the previous step. In this case, with respect to the adsorption cylinder (T3-1_4A/T6-1_4B) in the purge step, the supply flow path opening/closing unit (T3-1_2A/T6-1_2B) is in the closed state, the exhaust flow path opening/closing unit (T3-1_3A/T6-1_3B) is in the open state, and the communication flow path opening/closing unit (5) is in the open state. On the other hand, with respect to the adsorption cylinder (T3-1_4B/T6-1_4A) in the pressurized adsorption step, continuingly, the supply flow path opening/closing unit (T3-1_2B/T6-1_2A) is in the open state and the exhaust flow path opening/closing unit (T3-1_3B/T6-1_3A) is in the closed state. In the adsorption cylinder (T3-1_4A/T6-1_4B) in the purge step, the communication flow path opening/closing unit (5) is changed to the open state, which renders the adsorption cylinders (4A) and (4B) connected to each other at the ends of the concentrated oxygen gas outlet side, and a part of concentrated oxygen gas is flowed back as purge gas from the adsorption cylinder (T3-1_4B/T6-1_4A) in which the concentrated oxygen gas is produced in the pressurized adsorption step, to the other adsorption cylinder (T3-1_4A/T6-1_4B), thereby pushing out the desorbed nitrogen, resulting in enhancement of the desorption efficiency of nitrogen gas from the adsorbent in the depressurized desorption step (see FIG. 3(*b*)). In the adsorption cylinder (T3-1_4B/T6-1_4A) in the pressurized adsorption step, although the gas flow does not change from the previous step, the continuous supply of pressurized air increases the nitrogen adsorption on the adsorbent in the adsorption cylinder (T3-1_4B/T6-1_4A) to produce concentrated oxygen gas, and the produced concentrated oxygen gas is delivered to the concentrated oxygen gas tank (7) via the check valve (T3-1_6B/T6-1_6A) (see FIG. 3(*b*)). Although the time for T3-1/T6-1 may be any length as long as a required oxygen concentration can be obtained, it is preferable to set the time in such a way that the oxygen production is continued in the pressurization side adsorption cylinder, the adsorbed nitrogen is more desorbed in the depressurization side adsorption cylinder, and the desorbed nitrogen is completely exhausted.

Note that, although FIGS. 2(*a*) and 2(*b*) show an example, as a more preferable example, in which purging is performed in the second half of the depressurized desorption step, the purge step (T3-1/T6-1) may be omitted if the required oxygen concentration can be obtained without it. In addition, since the purge step (T3-1/T6-1) is a step in which a part of the concentrated oxygen gas produced in the adsorption cylinder during pressurized adsorption is supplied to the adsorption cylinder during depressurized desorption, the time for the depressurized desorption step (T2/T5), in which only depressurized desorption is performed, can be omitted and the control is performed as a purge step (T3-1/T6-1) in which the depressurized desorption and purging are performed at the same time if the required oxygen concentration can be obtained. In this case also, it is preferable to set the time in such a way that the oxygen production is continued in the pressurization side adsorption cylinder, and the desorbed nitrogen is completely exhausted in the depressurization side adsorption cylinder. Note that, although FIGS. 2(*a*) and 2(*b*) show "purge step" and "depressurized desorption step" as different steps such that the purge step (T3-1/T6-1) is performed after the depressurized desorption step (T2/T5), since the purging means to purge a part of the concentrated oxygen gas produced in the adsorption cylinder during pressurized adsorption to the adsorption cylinder during depressurized desorption, this is presumably one aspect in which the purge step is included in the depressurized desorption step, and therefore sometimes expressed as "performing purging in the second half of the depressurized desorption step".

T3-2/T6-2, as shown in FIG. 2(*b*), is a pre-pressurization step for one adsorption cylinder (T3-2_4A/T6-2_4B), and the other adsorption cylinder (T3-2_4B/T6-2_4A) continues the pressurized adsorption step of the previous step. In the pre-pressurization step of the adsorption cylinder (T3-2_4A/T6-2_4B), the exhaust flow path opening/closing unit (T3-2_3A/T6-2_3B) is switched from the open state in the previous step (depressurized desorption step to purge step) to the closed state. When the exhaust flow path opening/closing unit (T3-2_3A/T6-2_3B) is changed to the closed state, the already depressurized adsorption cylinder (T3-2_4A/T6-2_4B) is to start pressurization in advance of the next step of pressure equalization step, and the cylinder pressure of the adsorption cylinder (T3-2_4A/T6-2_4B) in a depressurized state can be increased in advance (FIG. 4(*b*)). In the adsorption cylinder (T3-1_4B/T6-1_4A) in the pressurized adsorption step, although the gas flow does not change from the previous step, the continuous supply of pressurized air maintains the pressure in the adsorption cylinder (T3-2_4B/T6-2_4A) and increases the nitrogen adsorption on the adsorbent to produce concentrated oxygen gas, and the produced concentrated oxygen gas is delivered to the concentrated oxygen gas tank (7) via the check valve (T3-2_6B/T6-2_6A) (see FIG. 3(*b*)). The time for T3-2/T6-2 can be adjusted depending on the required condition of pre-pressurization, and the time does not matter as long as the required oxygen concentration is obtained.

Through steps T1 to T6-2, one cycle of adsorption and desorption is completed in one adsorption cylinder, and by repeating this cycle, concentrated oxygen gas can be continuously produced. The cycle time does not matter as long as the concentration of produced oxygen reaches a specified value. As shown in FIG. 4(*b*), as a result of the pre-pressurization step in which the already depressurized inside is pressurized in advance in the adsorption cylinder (T1_4B/T4_4A), the depressurization-side adsorption cylinder can start the pressure equalization from the state of increased cylinder pressure, thereby preventing pressure drops in both cylinders in the pressure equalization step. As a result, the already depressurized adsorption cylinder (T1_4B/T4_4A) and the already pressurized adsorption cylinder (T1_4A/T4_4B) are pressure-equalized, and the equalized pressure becomes higher than by the conventional method, thereby preventing the discharge pressure drop of the pressurized air supply unit and the internal pressure drop of the concentrated oxygen gas tank. As a result, in the case of low flow rate operation, as long as the case allows the lowered compressor rotation speed, the compressor rotation speed is lowered and thus power consumption can be suppressed without worrying about the restriction of the minimum operating pressure of the pilot type solenoid valve. In addition, decrease in the rotation speed of the compressor enables suppression of overadsorption of oxygen that occurs when the extraction flow rate is low with respect to the amount of supplied air. On the other hand, since fluctuations in the internal pressure of the concentrated oxygen gas tank are reduced, fluctuations in product flow rate are also suppressed.

The present technology can be applied to any oxygen concentrator as long as being continuous-flow type, regardless of a stationary type or portable type.

| [Reference Signs List] | |
|---|---|
| 1 | Pressurized air supply unit |
| 2A, 2B | Supply flow path opening/closing unit |
| 3A, 3B | Exhaust flow path opening/closing unit |
| 4A, 4B | Adsorption cylinder |
| 5 | Communication flow path opening/closing unit |
| 6A, 6B | Check valve |
| 7 | Concentrated oxygen gas tank |

The invention claimed is:

1. An oxygen concentrator comprising:

a plurality of adsorption cylinders filled with an adsorbent that preferentially adsorbs nitrogen over oxygen;

a compressor for supplying pressurized air to the adsorption cylinders;

a supply flow valve for connecting the compressor and each of the adsorption cylinders and opening/closing a gas flow path of pressurized air;

an exhaust flow valve for opening/closing a gas flow path for exhausting gas from each of the adsorption cylinders;

a concentrated oxygen gas tank for storing concentrated oxygen gas produced by the plurality of adsorption cylinders;

a communication flow valve for connecting an end of each of the adsorption cylinders on a concentrated oxygen gas outlet side and passing therethrough a part of produced concentrated oxygen gas; and a pilot type solenoid valve being used in at least either of the supply flow valve or the exhaust flow valve, wherein the oxygen concentrator has a processor for performing opening/closing control of the supply flow valve, the exhaust flow valve, and the communication flow valve, and the processor is configured to perform control in each of the adsorption cylinders in such a way that the following steps are repeated in the order listed, (a) a pressurized adsorption step of adsorbing nitrogen in pressurized air on an adsorbent in an adsorption cylinder, of the plurality of adsorption cylinders, by supplying pressurized air, and extracting unadsorbed oxygen from an end on a concentrated oxygen gas outlet side of the adsorption cylinder;

(b) a pressure equalization step of equalizing pressures in the plurality of adsorption cylinders;

(c) a depressurized desorption step of depressurizing the adsorption cylinder, desorbing adsorbed nitrogen, and exhausting to outside air;

(d) a pre-pressurization step of starting in advance pressurization of an already depressurized adsorption cylinder; and (e) a pressure equalization step of equalizing pressures in the plurality of adsorption cylinders, and in such a way that, while (a) the pressurized adsorption step is performed in one or in a group of adsorption cylinders, (c) the depressurized desorption step and (d) the pre-pressurization step are performed in the other or the other group of adsorption cylinders, wherein the processor, during (d) the pre-pressurization step, is further configured to control the exhaust flow valve from a first one of the adsorption cylinders during pre-pressurization to a closed state, is configured to control the supply flow valve to a second one of the adsorption cylinders during pre-pressurization to a closed state, and is configured to control the communication flow valve to an open state.

2. The oxygen concentrator according to claim 1, wherein the processor, during (b) and (e) pressure equalization steps, is further configured to control all of supply flow valves, including the supply flow valve, for the plurality of adsorption cylinders to an open state.

3. The oxygen concentrator according to claim 1, wherein the processor, in a second half of (c) the depressurized desorption step, is further configured to control a part of concentrated oxygen gas produced in an adsorption cylinder during pressurized adsorption to be purged to an adsorption cylinder during depressurized desorption.

4. The oxygen concentrator according to claim 1, wherein the processor, during (c) the depressurized desorption step, is further configured to control the communication flow valve to a closed state.

5. The oxygen concentrator according to claim 4, wherein the processor, during (b) and (e) pressure equalization steps, is further configured to control the communication flow valve to the open state.

6. A control method of an oxygen concentrator for controlling pressures in a plurality of adsorption cylinders so as to prevent a drop in pilot pressure supplied to a pilot type solenoid valve used in at least either of a supply flow valve or an exhaust flow valve, wherein the control method comprises performing control in each of the adsorption cylinders in such a way that the following steps are repeated in the order listed, a pressurized adsorption step of adsorbing nitrogen in pressurized air on an adsorbent in an adsorption cylinder, of the plurality of adsorption cylinders, by supplying pressurized air to the adsorption cylinder from a compressor, and extracting unadsorbed oxygen from an end on a concentrated oxygen gas outlet side of the adsorption cylinder;

a pressure equalization step of equalizing pressures in the plurality of adsorption cylinders;

a depressurized desorption step of depressurizing the adsorption cylinder, desorbing adsorbed nitrogen, and exhausting to outside air;

a pre-pressurization step of starting in advance pressurization of an already depressurized adsorption cylinder; and a pressure equalization step of equalizing pressures in the plurality of adsorption cylinders, and in such a way that, while the pressurized adsorption step is performed in one or in a group of adsorption cylinders, the depressurized desorption step and the pre-pressurization step are performed in the other or the other group of adsorption cylinders, wherein the control method further comprises, during the pre-pressurization step, controlling the exhaust flow valve from a first one of the adsorption cylinders during pre-pressurization to a closed state, controlling the supply flow valve to a second one of the adsorption cylinders during pre-pressurization to a closed state, and controlling a communication flow valve to an open state.

* * * * *